United States Patent
Sabliov et al.

(10) Patent No.: US 9,220,787 B2
(45) Date of Patent: Dec. 29, 2015

(54) VITAMIN E CONJUGATES, AND THEIR USES AS ANTIOXIDANTS AND PRODRUG DELIVERY VEHICLES

(75) Inventors: Cristina M. Sabliov, Baton Rouge, LA (US); Carlos E. Astete, Baton Rouge, LA (US); David Spivak, Baton Rouge, LA (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 13/698,334

(22) PCT Filed: May 18, 2011

(86) PCT No.: PCT/US2011/036958
§ 371 (c)(1),
(2), (4) Date: Jan. 28, 2013

(87) PCT Pub. No.: WO2011/146589
PCT Pub. Date: Nov. 24, 2011

(65) Prior Publication Data
US 2013/0210702 A1    Aug. 15, 2013

Related U.S. Application Data

(60) Provisional application No. 61/346,517, filed on May 20, 2010.

(51) Int. Cl.
| | |
|---|---|
| A61K 38/00 | (2006.01) |
| A61P 11/00 | (2006.01) |
| A61K 47/48 | (2006.01) |
| C07D 311/58 | (2006.01) |
| C07D 403/12 | (2006.01) |

(52) U.S. Cl.
CPC ........ *A61K 47/48107* (2013.01); *C07D 311/58* (2013.01); *C07D 403/12* (2013.01); *Y10T 428/2982* (2015.01)

(58) Field of Classification Search
CPC ... A61K 2300/00; A61K 31/00; A61K 38/00; A61K 41/00; A61K 47/48123
See application file for complete search history.

(56) References Cited

U.S. PATENT DOCUMENTS

2002/0127252 A1   9/2002   Kramer ................. 424/401
2002/0165268 A1   11/2002  Wechter ................ 514/456

FOREIGN PATENT DOCUMENTS

| EP | 0238302 | 5/1992 |
| JP | 2003-267992 | 9/2003 |
| JP | 2008-19188 | 1/2008 |

OTHER PUBLICATIONS

Mustacich et al., Free Radical Biology & Medicine 41 (2006) 1069-1078.*
Wallert et al., (Free Radical Biology and Medicine, vol. 68, Mar. 2014, pp. 43-51).*
Mustacich et al., (Free Radical Biology & Medicine, 2006, 41, 1069-1078).*
Jewett, (The Effects of Alcohols as a Medicine, 1865).*
Mazzini et al., (Chirality, 2009, 21:519-524).*
Hosomi, A. et al., "Affinity for Alpha-Tocopherol Transfer Protein as a Determinant of the Biological Activities of Vitamin E Analogs," FEBS Lett, vol. 409, pp. 105-108 (1997).
Leonard, S.W. et al., "Incorporation of Deuterated RRR- or All-Rac-Alpha-Tocopherol in Plasma and Tissues of Alpha-Tocopherol Transfer Protein-Null Mice," American Journal of Clinical Nutrition, vol. 75, pp. 555-560 (2002).
Schuelke, M. et al., "Urinary Alpha-Tocopherol Metabolites in Alpha-Tocopherol Transfer Protein-Deficient Patients," J Lipid Res, vol. 41, pp. 1543-1551 (2000).
Stvolinsky, S.L. et al., "Biological Activity of Novel Synthetic Derivatives of Carnosine," Cell Mol Neurobiol, vol. 30, pp. 30, pp. 395-404 (2010) (published online Oct. 2, 2009).
Wang, Y.S. et al., "Synthesis of Alpha-Tocohexaenol (Alpha-T6) a Fluorescent, Oxidatively Sensitive Polyene Analogue of Alpha-Tocopherol," Bioorganic & Medicinal Chemistry, vol. 18, pp. 777-786 (2010).

* cited by examiner

*Primary Examiner* — Marcela M Cordero Garcia
*Assistant Examiner* — Kaipeen Yang
(74) *Attorney, Agent, or Firm* — John H. Runnels

(57) ABSTRACT

Tocopherol conjugates are disclosed that are useful as antioxidants or as pro-drug delivery vehicles. The conjugates are amphiphilic, and tend to localize at the interface between water domains and lipid domains. A prototype embodiment disclosed is an alpha tocopherol-linker-carnosine conjugate that has been designated VECAR.

17 Claims, No Drawings

VITAMIN E CONJUGATES, AND THEIR USES AS ANTIOXIDANTS AND PRODRUG DELIVERY VEHICLES

This is the United States national stage of international application PCT/US2011/036958, international filing date May 18, 2011, which claims the benefit of the May 20, 2010 filing date of U.S. provisional patent application Ser. No. 61/346,517.

TECHNICAL FIELD

This invention pertains to conjugates of vitamin E, and their uses as antioxidants or as pro-drug delivery vehicles.

BACKGROUND ART

Oxidative stress is linked with cardiovascular and other major diseases such as cancer, acute inflammation, Parkinson's, and Alzheimer's. In 2007, an estimated $430 billion was spent to treat 80 million people suffering from some type of cardiovascular disease. Antioxidant agents play a vital role in the defense against free radicals and oxidant molecules via radical scavenging, metal ion chelation, and co-antioxidant action. The balance between oxidative species and antioxidant systems defines the oxidative stress of a living system. The oxidative stress level determines when a biological system is at high risk for various diseases.

Atherosclerosis in particular has been related to oxidative processes. High levels of oxidant molecules, or low levels of antioxidants are linked to high oxidative stress that can trigger atherosclerosis. The "oxidation theory" of atherosclerosis considers free radicals to be precursors in development of the disease. Vitamin E, especially α-tocopherol, is a natural antioxidant present in the lipophilic phase of every cell. Among the lipophilic antioxidants, α-tocopherol is one of the most potent. Other important lipophilic antioxidants are coenzyme Q10 and the carotenoids.

Low-density lipoprotein (LDL) comprises a core of cholesterol and triglycerides, surrounded by a layer of fatty acids, cholesteryl esters, apolipoproteins, and phospholipids. The outer layer is more hydrophilic, while the core is more hydrophobic. Oxidation of LDLs has been associated with the development of atherosclerosis. The ox-LDL (i.e. the oxidized form of LDL) stimulates the host response and the formation of foam cells.

Lipophilic antioxidants inhibit oxidation of the lipid fraction of LDLs, but apolipoproteins are not protected from oxidation even in the presence of lipophilic antioxidants.

Hydrophilic antioxidants can protect hydrophilic molecules such as proteins, DNA, and carbohydrates from oxidation, and they can also regulate some oxidative molecules for signaling purposes. Examples of hydrophilic antioxidants include vitamin C and carnosine. Others include uric acid, and certain flavonoids, micronutrients, peptides, and proteins.

The dipeptide carnosine (β-alanyl-L-histidine) is known to have antioxidant properties, and also to suppress protein glycation and crosslinking. Carnosine has also been suggested as an agent for controlling secondary problems in diabetes.

Several synthetic antioxidants have been reported—e.g., butylated hydroxytoluene (BHT), butylated hydroxyanisole (BHA), propyl gallate; and vitamin E derivatives, including Trolox™, 3-oxa-chromanol derivatives, brominated alpha-tocopherol methanol-dimer, raxofelast, vitamin EC, and probucol. Several synthetic antioxidant molecules reported in the literature use the OH group of α-tocopherol to attach other molecules to α-tocopherol, or to modify the chromanol ring. These prior modifications have, however, decreased the specificity of the α-TTP interaction for α-tocopherol.

It has been suggested that α-tocopherol can act alternatively either as a pro-oxidant or as an anti-oxidant, and that this switch in behavior is induced by the level of oxidative stress. At low oxidative stress, α-tocopherol acts as a pro-oxidant, promoting lipid peroxidation. At high oxidative stress, α-tocopherol acts as an anti-oxidant. Co-antioxidants such as coenzyme Q-10 may play a role in promoting the anti-oxidant behavior of α-tocopherol. However, the pro-oxidant action of vitamin E has not yet been proven in mammals.

In vivo and in vitro assays have shown that Vitamin E is effective in protecting LDL from oxidation. However, clinical trials involving Vitamin E in patients with coronary artery disease or atherosclerosis have given conflicting results.

There is an unfilled need for new anti-oxidant compounds for the treatment and prevention of oxidative-stress-associated diseases.

Vitamin E

Vitamin E is a lipophilic vitamin with both antioxidant properties and non-antioxidant activities. The Vitamin E family includes four tocopherols (α, β, γ, δ) and four tocotrienols (α, β, γ, δ), the difference being that the tocotrienols have unsaturated phytyl chains. The differences between the α, β, γ, and δ compounds lie in the number and positions of the methyl groups on the aromatic ring of the tocopherol or tocotrienol.

The main antioxidant functions of vitamin E are to trap peroxyl radicals, and to break chain reactions of lipid peroxidation. Vitamin E also quenches superoxide anions ($O_2.^-$), singlet oxygen ($^1O_2$), and hydroxyl radicals (.OH); and vitamin E inhibits the reaction of nitric oxide (NO) with $O_2.^-$.

The antioxidant activity of tocopherols is related to the methylation pattern and to the number of methyl groups on the phenolic ring in the order: α>β>γ>δ.

Supplementation with vitamin E has not shown conclusive results in the prevention or control of diseases such as cardiovascular disease, cancer, or atherosclerosis, although clinical trials have suggested that some patients with pre-existing cardiovascular disease can benefit from supplementation with α-tocopherol (up to 800 IU/day or 537 mg/day).

Carnosine (β-Alanyl-L-Histidine)

Carnosine is a hydrophilic dipeptide (β-alanyl-L-histidine) that is synthesized exclusively by mammals. It is found in high concentrations in muscle and brain tissue, both of which can experience high oxidative stress. Human skeletal muscle levels of carnosine range from 2 to 20 mM. In the brain, carnosine is nonuniformly distributed with higher levels (up to 5 mM) in the olfactory epithelium and the bulbs. Carnosine and its analogs homocarnosine and anserine are degraded by the enzyme carnosinase, which is actually a group of intra- and extracellular dipeptidases.

The imidazole moiety of carnosine has been associated with the dipeptide's antioxidant properties. It has been suggested that the protons on the nitrogen ring and on the methylene carbon adjacent to the imidazole ring are required for antioxidant activity.

Carnosine can protect proteins from oxidation. Carnosine may also have beneficial effects in diabetes, and in certain neurodegenerative diseases that are associated with high levels of zinc, such as Alzheimer's disease.

Tatsunori et al., Japanese Patent Application Publication 2008019188A (English abstract, 2008) discloses a carnosine derivative and its use in medicines, skin cosmetics, and the like for treating or preventing diseases caused by damage due to active oxygen species, for preventing aging, and the like.

S. L. Stvolinsky et al., "Biological Activity of Novel Synthetic Derivatives of Carnosine," Cell Mol Neurobiol (2010) 30:395-404 (published online 2 Oct. 2009) discloses two derivatives of carnosine, (S)-trolox-L-carnosine and (R)-trolox-L-carnosine, having antioxidant properties.

See also: Y. S. Wang et al., "Synthesis of Alpha-Tocohexaenol (Alpha-T6) a Fluorescent, Oxidatively Sensitive Polyene Analogue of Alpha-Tocopherol," Bioorganic & Medicinal Chemistry (2010) 18:777-786; A. Hosomi et al., "Affinity for Alpha-Tocopherol Transfer Protein as a Determinant of the Biological Activities of Vitamin E Analogs," FEBS Lett (1997) 409:105-108; M. Schuelke et al., "Urinary Alpha-Tocopherol Metabolites in Alpha-Tocopherol Transfer Protein-Deficient Patients," J Lipid Res (2000) 41:1543-1551; and S. W. Leonard et al., "Incorporation of Deuterated RRR— or All-Rac-Alpha-Tocopherol in Plasma and Tissues of Alpha-Tocopherol Transfer Protein-Null Mice," American Journal of Clinical Nutrition (2002) 75:555-560.

DISCLOSURE OF THE INVENTION

We have discovered novel conjugates of vitamin E that are useful, for example, as antioxidants or as pro-drug delivery vehicles. The conjugates are amphiphilic, and tend to localize at the interface between water domains and lipid domains. Vitamin E is covalently conjugated with a hydrophilic antioxidant, for example carnosine, joined by a bio-stable linker. The resulting conjugates possess potent antioxidant properties, and can inhibit oxidation in polyunsaturated fatty acids (PUFAs) and LDL.

The limitations of lipophilic natural antioxidants have been overcome with the novel antioxidants, which may be formed by covalently conjugating a hydrophobic antioxidant with a hydrophilic antioxidant, joined by a bio-stable linker. The hydrophobic component, the hydrophilic component, or both may be natural-occurring antioxidants. The novel structure provides better antioxidant performance in both the hydrophilic and hydrophobic regimes (e.g., in both the hydrophilic and the hydrophobic portions of LDL particles). The novel structure affords synergetic effects from antioxidant-coantioxidant interactions. An important aspect of the novel compounds is that they maintain the biotransport properties that are inherent to natural α-tocopherol. Without wishing to be bound by this hypothesis, we expect the novel compounds to be recognized and transported in vivo by a specific transport protein, α-TTP, that ordinarily acts to transport α-tocopherol into LDLs. By contrast, modification of the hydroxyl group on the chromanol ring of an α-tocopherol derivative inhibits uptake of the derivative by α-TTP. On the other hand, modification of the phytyl chain, the linker, does not appear to affect recognition of α-tocopherol derivatives. We therefore chose the phytyl chain, the linker, as the site to introduce modifications with additional bioactive molecules, such as the hydrophilic antioxidant carnosine. Hydrophilic molecules such as carnosine are not expected to enter into lipophilic pathways in living systems. However, the novel compounds can shuttle such hydrophilic, bioactive molecules into LDL particles, molecules that ordinarily would not be localized there. The hydrophilic bioactive molecule is tethered to an α-tocopherol or vitamin E derivative via a bio-stable linker, such as an alkyl chain, a phytyl chain, or analog.

In one embodiment, conjugates in accordance with the present invention have the following general structure:

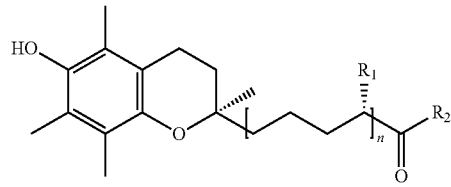

wherein:
n=from 1 to 18, more preferably from 2 to 5 (inclusive range in each case)

$R_1$=H or $CH_3$ $R_2$=antioxidant, drug, or other moiety of interest. $R_2$ will often be, but need not necessarily be, hydrophilic. Examples include the following compounds and their various derivatives and homologues: carnosine, lutein, vitamin C, cis-platin, flavonoids, resveratrol, co-enzyme Q, polyphenols, epicatechin (EC), epigallocatechin (EGC), epigallocatechin gallate (EGCG), gallic acid, gallic acid derivatives, fluorescent probes, coumarin 6, fluorescein sodium salt; and chemotherapeutic compounds such as abraxane, doxorubicin, herceptin, and paclitaxel; and derivatives of these compounds.

When a prodrug in accordance with the present invention is administered, whether orally, by injection, or other route of administration, it is processed in the liver by the enzyme alpha-tocopherol transfer protein, which mediates transfer of the drug to low density lipoprotein (LDL). The active drug molecule will then be sequestered (in whole or in part) in LDL, and thence distributed throughout the body via the bloodstream. Thus it can improve the bioavailability of a wide number of both hydrophilic and hydrophobic drugs.

While the lipophilic tocopherol will be internalized in the LDLs, we expect that the hydrophilic carnosine will tend to reside more toward the polar surface of the LDL particles. The complementary positioning of carnosine in polar regions of LDL particles may offer a unique and improved defense against oxidation as compared to vitamin E alone. Additionally, the novel compounds allow delivery of a hydrophilic antioxidant or other bioactive compound to LDLs that would otherwise not normally localize there.

Without wishing to be bound by this hypothesis, it is expected that the novel compounds will be recognized by the liver protein α-tocopherol transfer protein (α-TTP), which incorporates α-tocopherol into nascent LDL particles. The mechanism of action of α-TTP is not completely understood, but animal and clinical studies in patients deficient in α-TTP have shown that the protein is critical in achieving high plasma levels of α-tocopherol. Alpha-TTP has essentially 100% affinity for RRR-α-tocopherol, 38% affinity for β-tocopherol, 9% for γ-tocopherol, 2% for α-tocopherol acetate, and only 9% affinity for Trolox. We expect that the novel conjugates, which include an alkyl chain or phytyl chain (or analog) are readily recognized by α-TTP, and any drugs or other compounds covalently linked in the novel vitamin E conjugate should be readily transported by α-TTP.

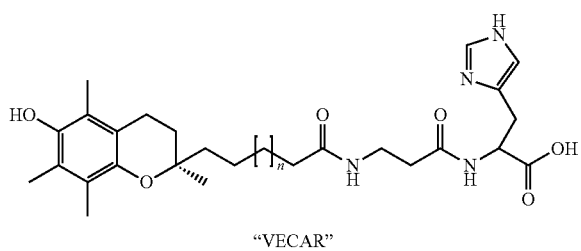

"VECAR"

In a prototype example, we have successfully synthesized a compound that we have designated "VECAR," a conjugate of Vitamin E and Carnosine, whose structure is shown above. We prepared VECAR through a multistep synthesis involving esterification, protection, and reduction reactions. The value of n in the VECAR structure is preferably from 8 to 18 (inclusive), and more preferably from 10 to 16 (inclusive), although n may also be higher or lower. In the prototype VECAR conjugate we have synthesized, n was 12. Optionally, one or more side-chain methyl groups could be attached along the $-(CH_2)_n-$ linker, analogously to the methyl groups found in the phytyl chain of the unmodified alpha-tocopherol molecule (the $R_1$ groups in the generalized structure previously depicted). (For clarification, note that the parameter "n" is used somewhat differently in different structures depicted in the present specification and claims.)

The novel VECAR conjugate possesses the beneficial antioxidant properties of both its alpha-tocopherol and the carnosine components. But it also possesses a synergy, so that it is truly more than a sum of its parts. The $-(CH_2)_n-$ covalent linker imparts minimal modification upon the conformation of either component, including the alpha tocopherol chromanol ring. Significantly, however, the $-(CH_2)_n-$ linker is itself a lipophilic domain, enhancing the compound's amphiphilic character. It is rather challenging to design a synthetic route to successfully incorporate a bio-stable linker into the conjugate, a linker that will help the entire molecule pass through and maintain proximity to polar areas of an LDL particle (such as the interface with water), without adversely affecting other portions of the conjugate. The alpha-tocopherol acts as both an antioxidant and as a carrier. The carnosine acts as a co-antioxidant, protecting proteins against oxidation.

VECAR or other conjugates in accordance with this invention may optionally be entrapped in nanoparticles, especially for biomedical uses such as delivery to the arterial wall for antioxidant defense against atherosclerosis. Such nanoparticles may be prepared through methods otherwise known in the art.

VECAR or other conjugates in accordance with this invention may also be used as a prodrug delivery system. Moieties other than carnosine can be attached to alpha tocopherol to treat various diseases. These moieties are not limited to antioxidants, and may include other drugs or compounds generally, including both lipophilic and hydrophilic compounds. These conjugates are particularly useful for delivering hydrophilic drugs into lipophilic domains, but are not limited to such uses; including, for example, antioxidants such as vitamin C, polyphenols, epicatechin, epigallocatechin, epigallocatechin gallate; fluorescent probes such as coumarin 6, fluorescein, or rhodamin; and chemotherapeutic drugs such as paclitaxel abraxane, doxorubicin, herceptin, derivatives of these compounds, and other chemotherapeutic drugs.

MODES FOR CARRYING OUT THE INVENTION

Antioxidant Activity

The amphiphilic structure of the conjugates causes them to localize at hydrophilic/lipophilic interfaces, for example in LDLs, where they can protect against oxidation. Vitamin E is a hydrophobic antioxidant that inhibits lipid oxidation. Carnosine is a hydrophilic antioxidant that inhibits oxidation of proteins. With its combined ability to protect both hydrophilic and hydrophobic components of LDLs, VECAR can prevent or ameliorate various oxidative-stress related diseases, such as atherosclerosis. No prior examples are known of amphiphilic antioxidant compounds that will position at the interface between hydrophobic and hydrophilic domains, and provide antioxidant protection for both domains at once.

Pro-Drug Activity

VECAR or other conjugates in accordance with this invention can also act as a pro-drug delivery system. Because the alpha-tocopherol moiety remains intact in the conjugate, the alpha-tocopherol moiety should be recognized by alpha-tocopherol transfer protein (alpha-TTP), which will enhance drug delivery.

Oxidative Theory of Atherosclerosis

One theory is that oxidative processes are associated with atherosclerosis. Oxidized LDL has been associated with atherosclerotic plaques. It is hypothesized that oxidative processes alter artery walls, causing monocytes and macrophages to be recruited from the bloodstream, along with excessive lipid deposition. As part of the process, LDL is oxidized within sub-endothelial spaces. The surface of LDL contains molecules such as apoB-100 protein, polar fatty acids, phospholipids, and unesterified cholesterol. A typical LDL composition is 20% phospholipids, 40% cholesterol esters, 20% protein, 10% unesterified cholesterol, 5% triglycerides, and 5% other lipophilic components. A typical size range for LDLs is from around 20 to around 26 nm.

An oxidized LDL particle can stimulate expression of adhesion molecules on endothelial cells, the LDL particle can itself be chemotactic, and it can regulate cell scavenger receptors. Wall thickening, vessel narrowing, and plaque formation can result in thrombosis and plaque rupture.

Vitamin E has been identified in LDL, where it is localized in the lipid phase. However, unmodified vitamin E does not provide strong protection against oxidative damage to apoB-100 on the surface of LDLs. Likewise, merely supplying a non-amphiphilic compound that possesses antioxidant activity (e.g., vitamin C) does not significantly increase protection. By modifying vitamin E with a hydrophilic moiety, the novel conjugate provides enhanced protection against oxidative damage to apoB-100 and other proteins.

In the novel antioxidants, the structure of the α-tocopherol derivative is maintained as closely as possible to that of the natural conformation, to better preserve the antioxidant properties of the α-tocopherol derivative and to better ensure that the derivative is recognized and transported by α-TTP. Any modifications are preferably made in the linker, which is apparently not a required moiety for the protein α-TTP to recognize α-tocopherol. To achieve these goals, it is preferred that the following three criteria should be observed: (1) The chromanol ring is not modified. (2) The linker (e.g., alkyl chain or phytyl chain) is sufficiently long to confer hydrophobic properties. (3) A second, preferably natural, antioxidant component is covalently linked, preferably at the end of the linker to maximize the separation between the hydrophilic and hydrophobic antioxidant moieties.

This novel approach allows molecules such as carnosine or vitamin C to be linked to α-tocopherol, so they can be introduced into LDLs and lipophilic sections of cells (i.e. the plasma membrane), for example by the action of α-TTP. Novel compounds in accordance with the present invention can provide substantially improved antioxidant properties as compared with their individual components (e.g., α-tocopherol or carnosine, whether alone or in a simple mixture). The novel compounds impart improved resistance against oxidation to LDL, and can help to treat or prevent oxidative-stress-associated diseases such as atherosclerosis.

The novel compounds can also treat or prevent neurodegenerative diseases, including but not limited to those associated with high levels of zinc; Alzheimer's and Parkinson's diseases; and various diseases associated with oxidative stress, including cardiovascular diseases such as atherosclerosis; and some cancers.

Initial in vivo animal trials will be conducted in accordance with all applicable laws and regulations in non-human mammals, followed by clinical trials to confirm activity in humans, in accordance with all applicable laws and regulations.

Methods for drug delivery known in the art may be used in administering compounds of the present invention to a human or other mammal. Compounds used in the present invention may be administered to a patient by any suitable means, including oral, intravenous, parenteral, subcutaneous, intrapulmonary, and intranasal administration. Parenteral infusions include intramuscular, intravenous, intraarterial, or intraperitoneal administration. The compounds may also be administered transdermally, for example in the form of a slow-release subcutaneous implant. They may also be administered by inhalation. Oral administration is preferred where feasible, for enhanced ease of delivery and enhanced patient compliance.

Pharmaceutically acceptable carrier preparations include sterile, aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. The active therapeutic ingredient may be mixed with excipients that are pharmaceutically acceptable and are compatible with the active ingredient. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like.

The form may vary depending upon the route of administration. For example, compositions for injection may be provided in the form of an ampoule, each containing a unit dose amount, or in the form of a container containing multiple doses.

A method for controlling the duration of action comprises incorporating the active compound into particles of a polymeric substance such as a polyester, peptide, hydrogel, polylactide/glycolide copolymer, or ethylenevinylacetate copolymers. Alternatively, an active compound may be encapsulated in microcapsules prepared, for example, by coacervation techniques or by interfacial polymerization, for example, by the use of hydroxymethylcellulose or gelatin-microcapsules or poly(methylmethacrylate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes. Alternatively, nanoparticles may be prepared through techniques known in the art.

As used herein, an "effective amount" of a compound or of a composition is an amount, that when administered to a patient (whether as a single dose or as a time course of treatment) ameliorates the effects of oxidative stress, or that successfully delivers the drug moiety from a prodrug conjugate; in each case where the desired effect occurs to a clinically significant degree; or alternatively, to a statistically significant degree as compared to control. "Statistical significance" means significance at the $P<0.05$ level, or such other measure of statistical significance as would be used by those of skill in the art of biomedical statistics in the context of a particular type of treatment or prophylaxis.

General Characterization Techniques for Antioxidants

Reactivity of the novel antioxidants, and that of conventional antioxidants for comparison, can be determined by any of several assays known in the art. These assays provide data about the rate of protection, free radical scavenging properties, affinity toward particular radicals or oxidant molecules, any pro-oxidant behavior, etc.

Assays that may be used to measure free radical scavenging properties include, for example, the DPPH assay and the ABTS assay. The 1,1-diphenyl-2-picryl hydrazyl (DPPH) radical is a stable free radical of purple color. Adding an antioxidant reduces the DPPH radical, which can be observed by color change (to yellow) in a spectrophotometer, for example by measuring absorbance at 518 nm. Mixing 2,2-α-azino-bis-(3-ethylbenzthiazoline-6-sulfonic acid) (ABTS) and hydrogen peroxide produces the ABTS radical (ABTS•). Subsequent incubation with peroxidase produces the radical cation ABTS•+. Adding an antioxidant causes an attenuation of the color change, which can be measured for example at 734 nm. The activity of an antioxidant is conventionally expressed as the concentration of an equivalent millimolar standard Trolox solution.

Superoxide anion scavenging properties can be evaluated, for example, by the xanthine-xanthine oxidase assay. A superoxide anion is formed by reaction between xanthine and xanthine oxidase. The superoxide anion can be detected, for example, at 560 nm via an induced color change in nitroblue tetrazolium (NBT). Alternatively, in the alkaline DMSO assay, alkaline DMSO is used to form superoxide anion, and reduction again may be monitored by spectroscopic observation of NBT at 560 nm, with and without the antioxidant molecule.

Hydroxyl radical scavenging properties can be measured, for example, by the p-nitroso dimethylaniline (pNDA) bleaching assay. The hydroxyl radical formed by Fenton's reaction of hydrogen peroxide with ferric chloride will bleach pNDA. The addition of an antioxidant changes the bleaching profile. Absorbance may be measured, for example, at 440 nm. Alternatively, in the deoxyribose assay, hydroxyl radical degrades deoxyribose, which can be measured colorimetrically.

Nitric oxide scavenging may be evaluated, for example, with nitroprusside. At physiological pH nitroprusside liberates nitric acid, which is converted to nitrous acid and subsequently forms nitrite ions on contact with air. The final reaction produces a pink color that may be measured at 546 nm.

Peroxynitrite scavenging performance can be determined by the tyrosine nitration assay. Peroxynitrite will nitrate tyrosine, which can be inhibited by the addition of an antioxidant molecule. Alternatively, the oxidation of dihydrorhodamine may be used in an assay, and its oxidation may be observed by fluorescence measurements.

The action of an antioxidant against lipid peroxidation may be evaluated by any of several methods known in the art. For example, the thiobarbituric acid assay (TBARS) is based on the reaction of melondialdehyde (MDA), an end product of lipid peroxidation, with thiobarbituric acid. The iodometric assay may be used for PUFA peroxidation and protein peroxidation studies. The iodometric assay is based on the ability of iodide to reduce hydroperoxides formed in lipid peroxidation. Other techniques include the use of conjugated dienes, fluorescence techniques, protein fragmentation coupled with SDS-PAGE, measuring surface charges by observing the electrophoretic mobility of Apo B-100, electron spin resonance (ESR), nuclear magnetic resonance (NMR), etc.

Other assays known in the art are generally used for in vivo measurements, such as measuring the total reactive antioxidant potential (TRAP), total antioxidant activity (TAA), oxygen radical absorbing capacity (ORAC), and total antioxidant reactivity (TAR).

Outline of Certain Experimental Work

Following is an outline of some of the experimental work that we have conducted to date:
a. Synthesis of vitamin E-carnosine: Synthesis of VECAR (with a 12-carbon linker chain). The synthesis employed protection of the OH group, activation of the carbonyl group, a Wittig reaction to form an ylide, attachment of carnosine, and de-protection of the OH group.
b. Characterization of the structure of the synthesized VECAR by nuclear magnetic resonance (NMR) and analytic thin-layer chromatography (TLC).
c. Testing the antioxidant properties of VECAR by DPPH and TBARS.

EXAMPLE 1

Materials

The following chemicals were purchased from Acros Organics: Trolox™ 97%, tert-butylchlorodimethylsilane 98%, and triethylamine 99%.

Methanol anhydrous 99.8%, imidazole >99.5% (GC), dimethylformamide anhydrous 99.8%, diisobutylaluminum hydride (DIBAL) 1.0 M solution in hexane, 12-bromododecanoic acid 97%, acetonitrile anhydrous 99.8%, triphenylphosphine 99%, tetrahydrofuran >99.9%, lithium bis(trimethylsilyl)-amide (LiHMDS) 1.0 M solution in tetrahydrofuran, palladium (Pd/C) 10 wt. % (dry basis) on activated carbon, wet, Degussa type E101 NE/W, L-carnosine 99%, and 4-(dimethylamino)pyridine (DMAP) 99% were purchased from Sigma-Aldrich.

Thionyl chloride 99+% and magnesium sulfate 99.5% were purchased from Alfa Aesar.

Compounds purchased from Mallinckrodt Chemicals were methanol, ethyl acetate, toluene, ammonium chloride, chloroform, sodium hydroxide, and sodium bicarbonate.

Dichloromethane, and hexanes (95% n-hexane) were purchased from J. T. Baker.

Silica gel, porosity: 60 Å, particle size: 40-63 μm, surface area: 500-600 m²/g, pH range: 6.5-7.5, and silica gel of 300 Å porosity were purchased from Sorbent Technologies.

O-benzotriazole-N,N,N',N'-tetramethyl-uronium-hexafluoro-phosphate (HBTU), 99.58% was purchased from ChemPep Inc.

The following compounds were purchased from Fisher Chemical: 1-propanol and sodium chloride. Sodium bicarbonate was purchased from EMD Chemicals.

A stock solution of DPPH in methanol, 0.4 mM was prepared and stored in the dark at −20° C. prior to use. A test sample was diluted with water (pH=3.5 prepared by addition of acetic acid) to 1 ml. The sample was then added to the dilute DPPH stock in methanol to obtain a final sample volume of 2 ml with a 0.1 mM DPPH concentration. The water:methanol ratio was 1:1 (v/v). A blank was prepared with 1 ml of water (pH=3.5) and pure methanol. Controls were prepared for each sample, with 1 ml of water (pH=3.5) and 1 ml of DPPH in methanol solution. Absorption readings were taken after 30 min at 518 nm using a Geminys 6 spectrophotometer (Thermo Scientific, Waltham, Mass.). The formula used to calculate the change in oxidation activity was $$\% \text{ change in activity} = ((\text{AbS}_{control} - \text{AbS}_{sample})/\text{AbS}_{control}) * 100\%$$

Synthesis of α-Tocopherol-Carnosine (VECAR)

EXAMPLE 2

Methyl Ester of Trolox™

The synthesis of α-tocopherol-Carnosine (VECAR) began with 6-hydroxy-2,5,7,8-tetramethylchroman-2-carboxylic acid (Trolox™). Trolox™ is a vitamin E derivative lacking the phytyl chain, thus rendering the compound hydrophilic. S-Trolox™ (3.5 g, 14 mmol) and dry methanol (26 mL) were stirred at 0° C. for 15 minutes. Thionyl Chloride (1.26 mL, 16.9 mmol) was added to the solution, which was then stirred at 0° C. for an additional 10 minutes. The solution was refluxed for 1 hour at 70° C. Triethylamine (4 mL, 11 mmol) was added after 15 minutes. The solvent was evaporated and the crystals were re-dissolved in methanol. The re-crystallization from methanol yielded white crystals (2.89 g, 80%). $^1$H (CDCl$_3$) NMR δ 4.24 (s, 1H, OH), 3.86 (s, 3H, OCH$_3$), 2.63 (m, 2H), 2.51 (m, 1H), 2.19 (s, 3H), 2.17 (s, 3H), 2.07 (s, 3H), 1.87 (m, 1H), 1.60 (s, 3H).

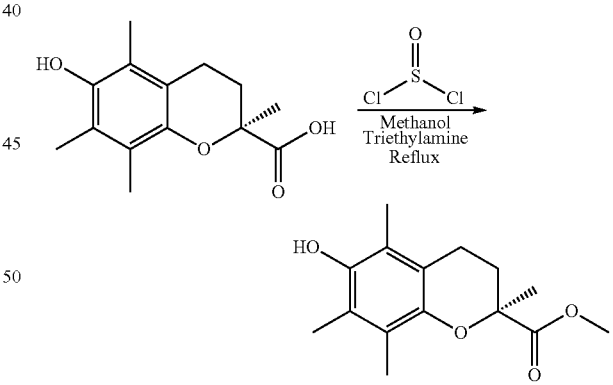

Figure 0-1: (S)-6-hydroxy-2,5,7,8-tetramethylchroman-2-carboxylic acid (Trolox) esterification

EXAMPLE 3

Protecting the Hydroxyl Group

The product of the first reaction, (S)-methyl-6-hydroxy-2,5,7,8-tetramethylchroman-2-carboxylate (S1) (1.254 g, 4.7 mmol), was mixed with tert-butyldimethylsilyl chloride (1.081 g, 7.2 mmol), and imidazole (1.339 g, 19.7 mmol) in dry dimethylformamide (10 mL). The mixture was stirred and heated in an oil bath under argon at 85° C. for 5 h, at which point none of the starting material S1 was detected by TLC. The reaction mixture was poured into water and then extracted with ethyl acetate. The solution was dried over magnesium sulfate. Evaporation yielded a light yellow oil. The crude product was purified by column chromatography on silica gel using (CH$_2$Cl$_2$:hexane=3:1). The yield of S2 was 1.62 g (90%). $^1$H NMR (CDCl$_3$) δ 3.66 (s, 3H, OCH$_3$), 2.62 (m, 2H), 2.44 (m, 2H), 2.15 (s, 3H), 1.87 (m, 3H), 1.85 (m, 1H), 1.60 (s, 3H), 1.04 (s, 9H), 0.12 (s, 6H).

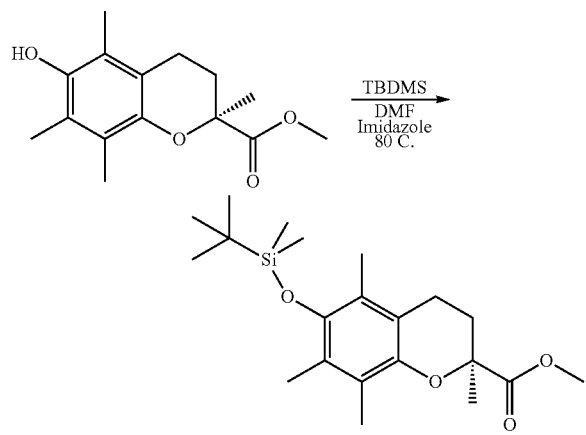

Figure 0-2: Synthesis of (S)-methyl 6-(tert-butyldimethylsilyloxy)-2,5,7,8-tetramethylchroman-2-carboxylate (S2) to protect the hydroxyl group in position 6.

EXAMPLE 4

Reducing the Ester to an Aldehyde

S2 (3.282 g, 8.67 mmol) was added to dry hexane (35 mL), and the mixture was cooled in an acetone/dry ice bath to −75° C. Diisobutylaluminum hydride (DIBAL-H, 1.0 M in hexane, 16 mL, 16 mmol) was added using a syringe such that the temperature of the reaction mixture did not exceed −70° C. After 2 h the reaction was quenched with dry methanol (10 mL), and stirred for 15 minutes. The solution was removed from the acetone/dry ice bath and allowed to warm to −8° C. Water (15 mL) was added to the solution by syringe. The solution was then poured into water, which was then extracted with hexane/ethyl acetate (2:1). The solution was dried over magnesium sulfate, and the solvent was evaporated. The crude product was purified by column chromatography using CH$_2$Cl$_2$:hexane (1:1 to 3:1). The yield of S3 was 2.33 g (77%). $^1$H NMR (CDCl$_3$) δ 9.63 (s, 1H), 2.56 (m, 2H), 2.28 (m, 1H), 2.17 (s, 3H), 2.12 (s, 3H), 2.08 (s, 3H), 1.84 (m, 1H), 1.39 (s, 3H), 1.05 (s, 9H), 0.12 (s, 6H).

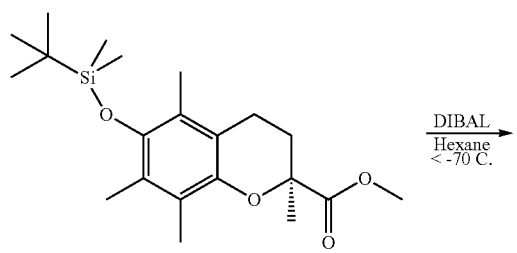

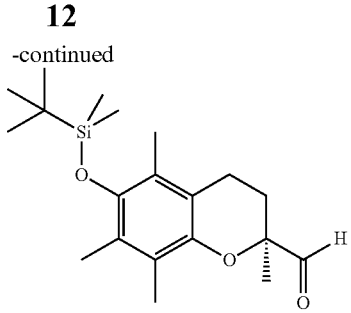

Reduction of S2 ester to synthesize (S)-6-(tert-butyldimethylsilyloxy)-2,5,7,8-tetramethylchroman-2-carbaldehyde (S3).

EXAMPLE 5

Ylide Synthesis

A solution of 12-bromododecanoic acid (1.66 g, 5.9 mmol) in dry acetonitrile (13 mL) was heated and stirred. Triphenylphosphine (1.637 g, 6.2 mmol) in dry acetonitrile (13 mL) was heated and stirred, and then added to the 12-bromododecanoic acid solution. The mixture then refluxed overnight. The solvent was removed. The crystals were dissolved in DCM (14 mL). Toluene (40 mL) was added, and the solution was stirred and heated to remove the DCM. The solution was cooled and the crystallized phosphonium salts were removed by filtration. The solution was decanted with toluene. The yield of S4 was 3.01 g (93.5%). $^1$H NMR (CDCl$_3$) δ 7.84-7.68 (m, 15H), 3.68-3.50 (m, 4H), 2.36 (s, 2H), 1.61-1.19 (m, 16H).

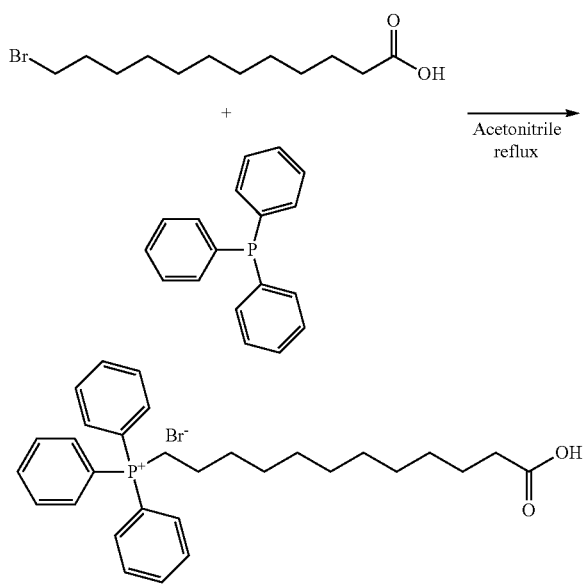

Reaction to synthesize (11-carboxyundecyl)triphosphonium bromide (S4) salt.

EXAMPLE 6

Wittig Reaction to Couple the Alkyl Chain

The phosphonium salt S4 (2.927 g, 5.4 mmol) was dissolved in dry THF (55 mL) at room temperature under argon.

A solution of LiHMDS in THF (1M in THF, 16 mL, 13.4 mmol) was added dropwise via syringe. The red glide was stirred for 2 h under argon. A solution of S3 (1.85 g) in dry THF (8 mL) was added dropwise. The color changed from red to pale yellow. The suspension was stirred for an additional 3 h, until S3 could no longer be found by TLC. The reaction was quenched with saturated NH$_4$Cl (80 mL) and water (80 mL), and then extracted with ethyl acetate. The solution was dried over magnesium sulfate. After solvent removal, trituration with cold hexane removed triphenylphosphine oxide. The hexane solution was evaporated, and the crude product was purified by column chromatography on silica gel using ethyl acetate:hexane (1:1). Yield of S5 was 1.99 g (71%). $^1$H NMR (CDCl$_3$) δ 5.32 (d, 2H), 2.55 (t, 2H), 2.35 (m, 1H), 2.11 (s, 8H), 2.09 (s, 2H), 2.04 (s, 3H), 1.64 (m, 2H), 1.46 (s, 4H), 1.24 (s, 9H), 1.04 (s, 9H), 0.11 (s, 6H).

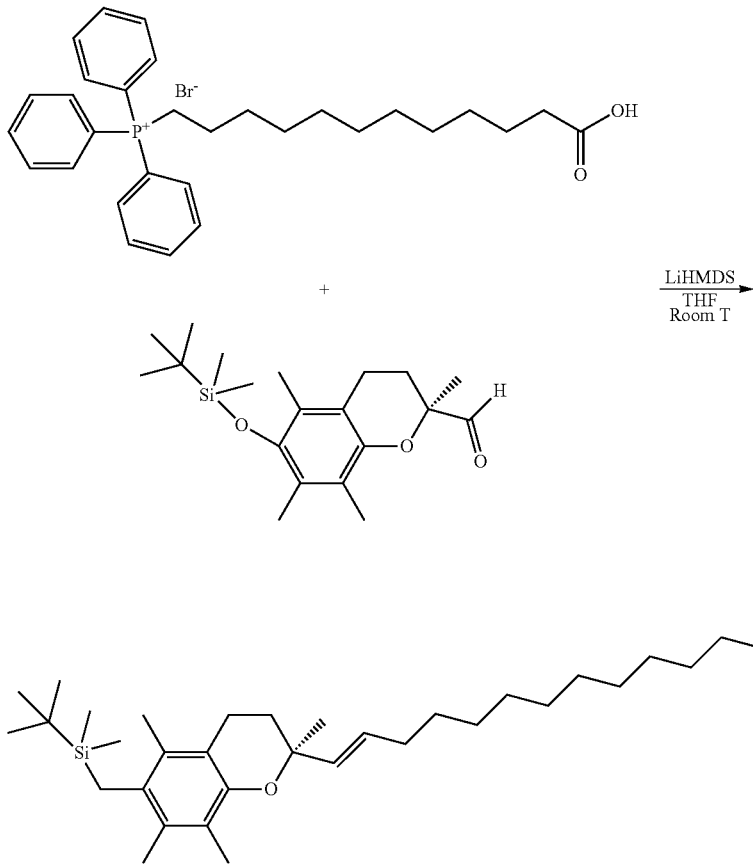

Wittig reaction to synthesize (S,E)-13-(6-(tert-butyldimethylsilyloxy)-2,5,7,8-tetramethylchroman-2-yl)tridec-12-enoic acid (S5).

EXAMPLE 7

Saturation of the Alkyl Chain

Pd/C (0.505 g) was added to a solution of S5 (0.95 g, 3.67 mmol) in ethyl acetate (85 mL). A hydrogen balloon was attached to the reaction mixture, which was then stirred for 18 h at room temperature. The mixture was filtered and evaporated to obtain S6 as an oil. The crude product was purified by column chromatography using hexane:ethyl acetate (4:1). The Yield of S6 was 0.91 g (94%). $^1$H NMR (CDCl$_3$) δ 2.55 (t, 2H), 2.37 (t, 2H), 2.07 (t, 9H), 1.80 (m, 2H), 1.58 (m, 2H), 1.22 (s, 18H), 1.05 (s, 9H), 0.12 (s, 6H).

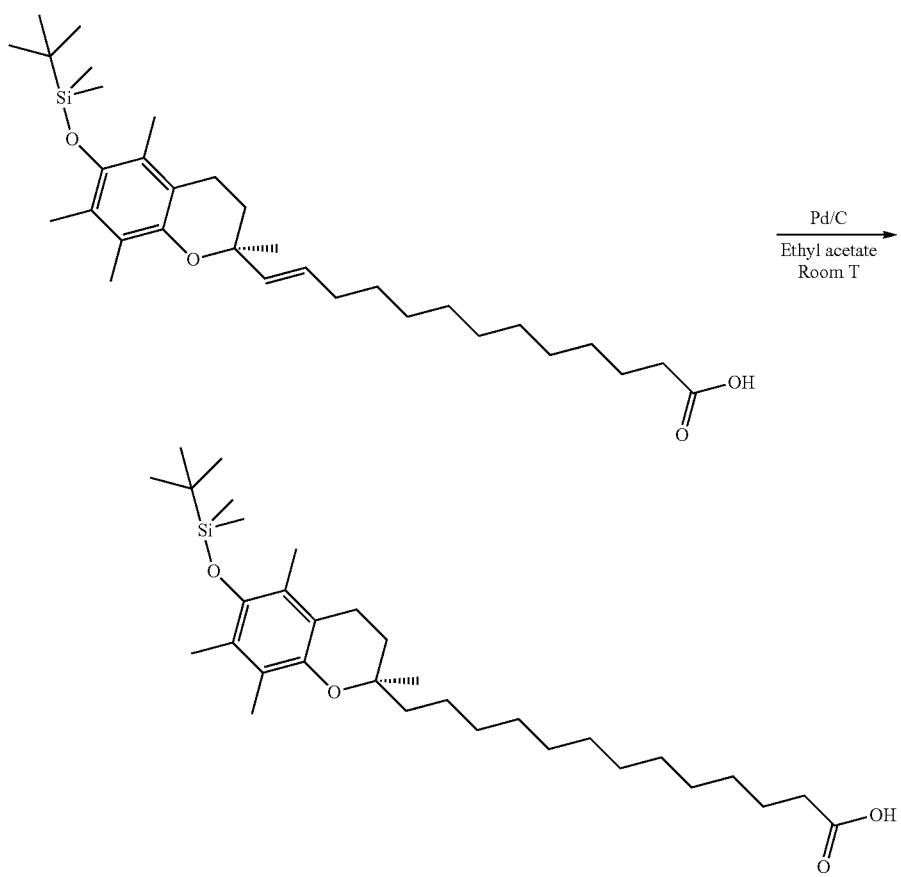

Saturation reaction to synthesize (R)-13-(6-(tert-butyldimethylsilyloxy)-2,5,7,8-tetramethylchroman-2-yl)tridecanoic acid (S6).

EXAMPLE 8

Carnosine Methyl Ester Dihydrochloride

Thionyl chloride (0.25 mL, 3.3 mmol) was added dropwise to a suspension of carnosine (602.9 mg, 2.7 mmol) in anhydrous methanol (24 mL) at 0° C., and the mixture was stirred for 10 minutes. The solution was refluxed at 75° C. for 1 hour, cooled to room temperature, and concentrated. The product, methyl 2-(3-aminopropanamido)-3-(1H-imidazol-4-yl)propanoate dihydrochloride (S7), was used in the next step without further purification. $^1$H NMR (MeOH) δ 8.85 (s, 1H), 7.67 (s, 1H), 7.55 (s, 1H), 4.82 (m, 3H), 3.94 (s, 3H), 3.30 (m, 2H), 3.01 (m, 2H), 2.70 (m, 2H).

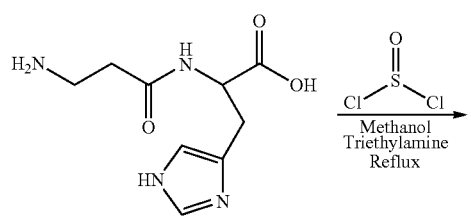

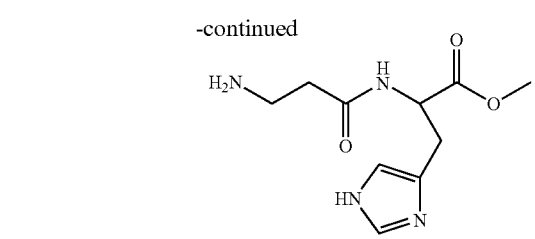

EXAMPLE 9
Coupling Carnosine Methyl Ester with Carboxylic Acid

The carboxylic acid compound S6 (840 mg, 1.59 mmol), DMAP (19 mg, 0.16 mmol), the carnosine-methyl ester hydrochloride (S7) (662 mg, 2.39 mmol), and triethylamine (1.67 mL, 5 equiv) were added to anhydrous DMF (13.4 ml). The solution was cooled to 0° C. in an ice bath. HBTU (721 mg, 1.9 mmol) in anhydrous DMF (3 mL) was added to the reaction mixture dropwise, with stirring for an additional 20 minutes at 0° C. The reaction was then stirred at room temperature overnight. Next, the solvent was evaporated and dried under high vacuum. The washing and extraction steps were performed with chloroform and water (without magnesium sulfate). The organic phase was collected and evaporated under vacuum. The purification was performed on a reverse phase silica gel ($C_{18}$, 300 Å pore size) using a mixture of methanol:water (7:3) as eluent. The yield of methyl 2-(3-(13-((R)-6-(tert-butyldimethylsilyloxy)-2,5,7,8-tetramethylchroman-2-yl)tridecanamido)propanamido)-3-(1H-imidazol-4-yl)propanoate (S8) was 0.62 g (43%). $^1$H NMR (MeOH) δ 8.52 (s, 1H), 7.24 (s, 1H), 3.74 (m, 3H), 2.57 (m, 2H), 2.41 (m, 2H), 2.09 (m, 13H), 1.78 (m, 2H), 1.58 (m, 4H), 1.52 (m, 4H), 1.27 (s, 15H), 1.22 (s, 4H), 1.04 (s, 9H), 0.11 (s, 6H)

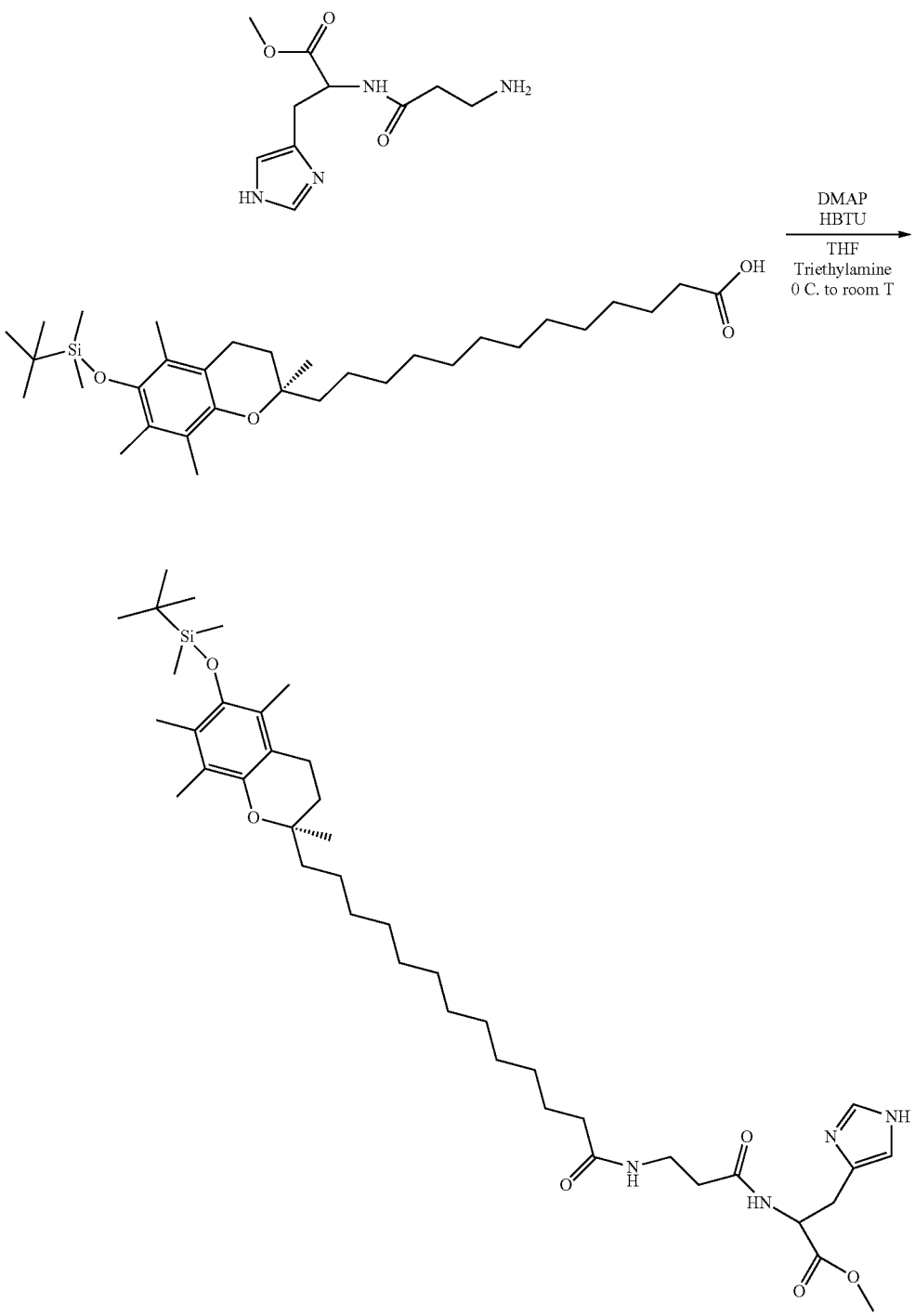 [SMILES: COC(=O)C(Cc1c[nH]cn1)NC(=O)CCN ; Cc1c(C)c2c(c(C)c1O[Si](C)(C)C(C)(C)C)CC[C@@](C)(CCCCCCCCCCCCC(=O)O)O2 ; COC(=O)C(Cc1c[nH]cn1)NC(=O)CCNC(=O)CCCCCCCCCCCC[C@]1(C)CCc2c(C)c(O[Si](C)(C)C(C)(C)C)c(C)c(C)c2O1]

EXAMPLE 10

De-Protection of the Hydroxyl Group of the Chromanol Ring

The de-protection of (S8) was performed by dissolving S8 (260 mg) in dry THF (10 ml), and adding TBAF (2.9 mL of a 1M THF solution) dropwise via syringe. The solution was stirred for 1.5 hour at room temperature. The THF was evaporated and replaced with chloroform (200 ml). The solution was washed with water three times. The crude VECAR product was purified by flash chromatography on reverse phase silica gel (60 Å pore size) using gradient elution with methanol:water (30%), and with methanol:water:ammonium hydroxide (8:1:1). The first two fractions collected the impurities, and pure VECAR was collected in the last fraction. The yield of VECAR was 130 mg (60%).

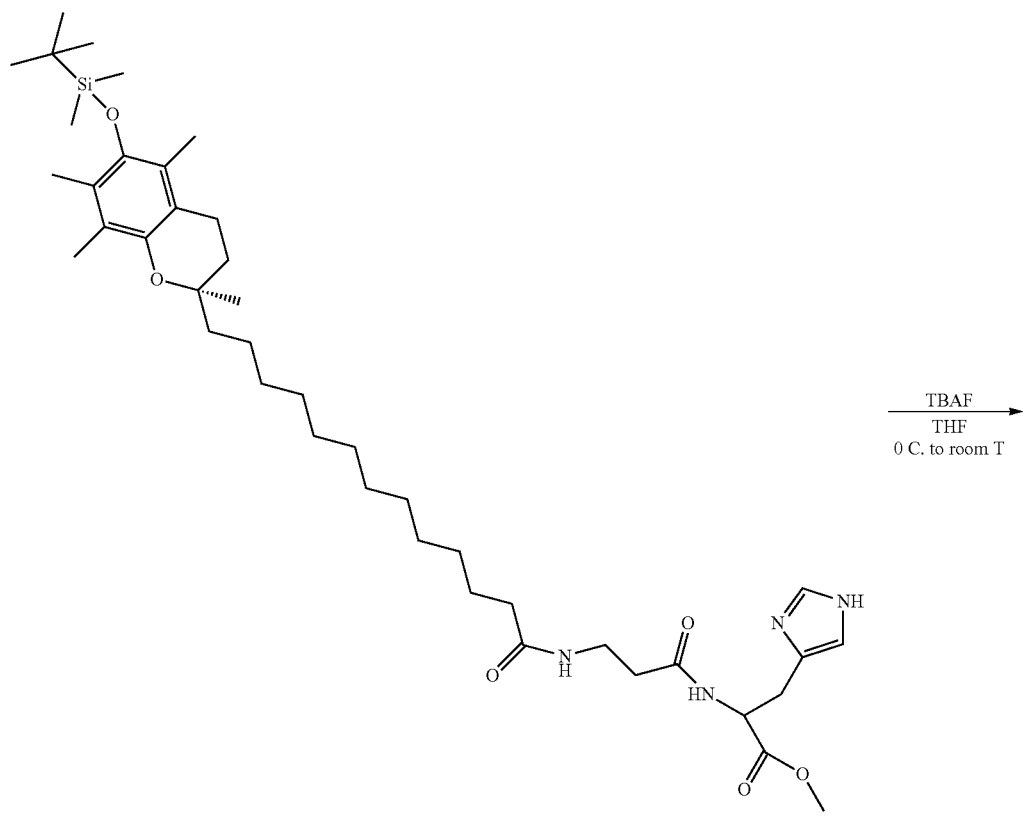
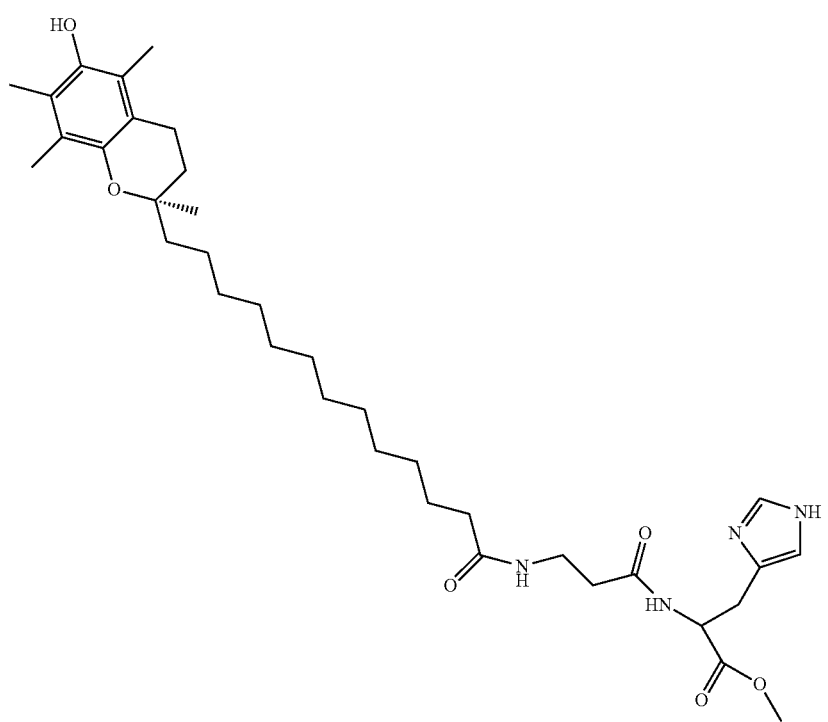

De-protection of S0 to synthesize methyl 2-(3-(13-((R)-6-hydroxy-2,5,7,8-tetramethylchroman-2-yl)tridecanamido) propanamido)-3-(1H-imidazol-4-yl)propanoate (VECAR).

EXAMPLE 11

Reverse Phase Silica Gel

Reverse phase silica gel was prepared for purifying the VECAR following the coupling reaction. Normal phase silica gel (100 mg) was suspended in toluene (500 ml), and 21 ml (0.52 mol) of octadecyltrichlorosilane ($C_{18}$, ODTS) was added dropwise. After 10 min, triethylamine (28 ml, 4 equiv.) was added to the suspension, and the final suspension was refluxed for 24 hr at 125° C. Finally, the reverse phase silica gel was washed with toluene (1 L), DCM (1 L), ethyl acetate (1 L), and methanol (4 L). The product was dried under high vacuum and stored until use.

EXAMPLE 12

Antioxidant Activity of VECAR Assayed by DPPH

The antioxidant behavior of VECAR was studied by DPPH assay. Measurements were performed at 5 concentrations to determine $IC_{50}$, the point at which 50% of DPPH had been reduced by VECAR. The $IC_{50}$ for VECAR was determined as 24.9±1.4 µM, nearly identical to the value of 24.4±1.5 µM for alpha-tocopherol.

Synthesis of VECAR—Summary and Discussion

The synthesis of VECAR, an amphiphilic derivative of carnosine and alpha-tocopherol with a bio-stable alkyl linker, was accomplished in nine steps. The steps were designed to form an alkyl linker with a reactive end group (a carboxylic acid). The first step (Trolox esterification) was performed by an acid chloride (thionyl chloride) reaction. The selection of the catalyst was based on yield and reaction time, as compared with those seen using p-toluenesulfonic acid as catalyst. The yields increased from 50% to 78% and the time was reduced from 18 hrs to less than 2 hrs when thionyl chloride was used as catalyst instead. The second step was to protect the hydroxyl group in the chromanol ring of Trolox with tert-butyldimethylsilyl chloride (TBDMS). This protection allowed the hydroxyl group to be recovered at the end of the synthesis. The third step was reduction of the acid to an aldehyde using DIBAL at −70° C. This reaction was difficult, because separation of the unreacted ester from the aldehyde required gradient elution-column chromatography. Any water present in the sample would reduce yields and increase the complexity of purification by flash chromatography. The reaction yields of the first three steps were improved by eliminating as much residual water in the samples as feasible.

Next, a Wittig reaction added a 12-carbon alkyl chain to the chromanol ring. The alkyl chain was provided by 12-bromododecanoic acid, from which a phosphonium salt was prepared prior to the Wittig reaction. The product was then saturated in the presence of hydrogen. The coupling reaction with carnosine was complicated due to the hydrophobic/hydrophilic behavior of the new molecule. The carnosine molecule was therefore modified to an ester, both to improve its solubility in polar solvents and to avoid reactions between the carboxylic group of carnosine either with the alpha-tocopherol derivative intermediate, or with the carnosine's own amino terminus. Different coupling reactions were tried, including those with dicyclohexylcarbodiimide (DCC), various conjugated anhydrides, and (2-(1H-Benzotriazole-1-yl)-1,1,3,3-tetramethyluronium hexafluorophosphate) (HBTU). The best results were obtained using HBTU as coupling reagent, with purification by reverse phase column chromatography. Reverse phase silica gel was used because the molecule did not move well through normal silica gel. Finally, the hydroxyl group was de-protected, using tetrabutylammonium fluoride (TBAF) to eliminate TBDMS. Not only were the reaction times reduced substantially, from overnight (12 hrs) to 1.5 hr, but the final purity of the VECAR also improved significantly. Reverse phase silica was used in flash column chromatography to purify the VECAR following the coupling reaction and de-protection. The structure of VECAR was confirmed by H-NMR.

The linker chain (which can optionally be used for the attachment of other molecules as well), preserved the antioxidant properties of the alpha-tocopherol portion of the VECAR molecule. As measured by the DPPH assay, the VECAR $IC_{50}$ value (24.9±1.4 µM) was quite close to that of pure alpha-tocopherol (24.4±1.5 µM).

In Vitro and In Vivo Studies

Diseases such as Parkinson's, Alzheimer's, and atherosclerosis are linked to oxidation processes and should benefit from VECAR. In vitro and in vivo studies will be performed to confirm VECAR's ability to protect LDLs from oxidation, and its ability to act as a transport vehicle to improve the bioavailability of other hydrophilic drugs and other compounds.

Optional embodiments include the following: HPLC analysis of tissue/blood/LDL distribution; or synthesis of a "VEPROBE" compound, in which the carnosine moiety of VECAR is replaced by a fluorescent probe (or other probe or reporter), to assist in the analysis of tissue/blood/LDL distribution.

In vivo studies will be performed with a VEPROBE compound to demonstrate the preferential uptake of the vitamin E-linked fluorescent probe as compared to the free fluorophore. The preferential uptake is an indicator of the improved bioavailability of the linked drugs or other compounds, presumptively resulting from α-TTP recognition. For example, confocal microscopy and direct quantitation techniques (such as HPLC) will be employed to determine plasma concentration and tissue distribution of the fluorophore, both when administered in free form and in the linked VEPROBE form.

The ability of VECAR to act against lipid peroxidation is demonstrated and quantitated by various methods. For example, the thiobarbituric acid assay (TBARS) is based on the reaction of melondialdehyde (MDA), which is an end product of lipid peroxidation with thiobarbituric acid. An iodometric assay can be used to quantify PUFA peroxidation and protein peroxidation, based on the ability of iodide to reduce the hydroperoxides that are formed in lipid peroxidation. Other common techniques that may be used to demonstrate the antioxidant activity of VECAR are measuring the total reactive antioxidant potential (TRAP), the total antioxidant activity (TAA), the oxygen radical absorbing capacity (ORAC), and the total antioxidant reactivity (TAR). These assays can be performed either in vitro on VECAR-enhanced LDLs, or in vivo by testing the plasma of animals or patients who have been given VECAR supplements. For example, it will be demonstrated that VECAR protects LDL from oxidation in vivo by showing that animals given a high-fat, atherogenic diet will nevertheless exhibit lower plasma TBARS values when the diet is supplemented with VECAR.

The complete disclosures of all references cited in the specification are hereby incorporated by reference. Also incorporated by reference is the complete disclosure of the priority application, U.S. provisional application Ser. No. 61/346,517, filed 20 May 2010, and of all references cited in the priority application. In the event of an otherwise irreconcilable conflict, however, the present specification shall control.

What is claimed:

1. The compound VECAR, wherein VECAR has the structure:

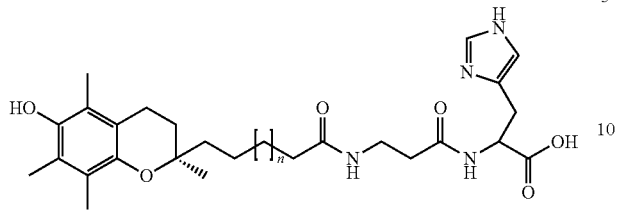

wherein n is an integer from 8 to 18.

2. A nanoparticle, wherein said nanoparticle comprises the compound VECAR of claim 1, wherein the diameter of said nanoparticle is between about 20 nm and about 5 μm.

3. A plurality of nanoparticles as recited in claim 2.

4. A method of treating or preventing a disease in a mammal, wherein the disease is associated with oxidative stress, said method comprising administering to the mammal an effective amount of the compound VECAR of claim 1.

5. The method of claim 4, wherein the disease is selected from the group consisting of atherosclerosis, cardiovascular disease, cancer, Alzheimer's disease, Parkinson's disease, and sequelae of aging.

6. A compound having the structure:

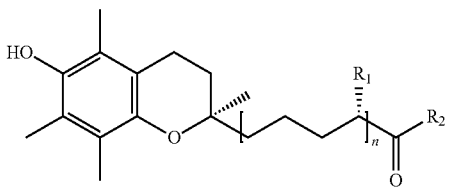

wherein:
n is an integer from 1 to 18;
$R_1$=H or $CH_3$, wherein any of the various $R_1$ groups may be the same as or different from any of the other $R_1$ groups;
$R_2$ is an antioxidant or drug.

7. A nanoparticle, wherein the diameter of said nanoparticle is between about 20 nm and about 5 μm; and wherein said nanoparticle comprises a compound having the structure:

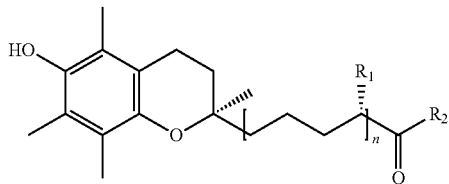

wherein:
n is an integer from 1 to 18;
$R_1$=H or $CH_3$, wherein any of the various $R_1$ groups may be the same as or different from any of the other $R_1$ groups;
$R_2$ is an antioxidant, drug, precursor, label, probe, or reporter.

8. A plurality of nanoparticles as recited in claim 7.

9. A method of treating or preventing a disease in a mammal, wherein the disease is associated with oxidative stress, said method comprising administering to the mammal an effective amount of a compound having the structure:

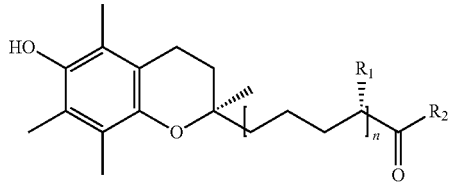

wherein:
n is an integer from 1 to 18;
$R_1$=H or $CH_3$ wherein an of the various $R_1$ groups may be the same as or different from any of the other $R_1$ groups;
$R_2$ is an antioxidant, drug, precursor, label, probe, or reporter.

10. The method of claim 9, wherein the disease is selected from the group consisting of atherosclerosis, cardiovascular disease, cancer, Alzheimer's disease, Parkinson's disease, and sequelae of aging.

11. The compound of claim 6, wherein n is an integer from 2 to 5.

12. A compound having the structure:

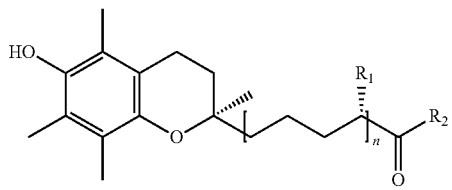

wherein:
n is an integer from 1 to 18;
$R_1$=H or $CH_3$, wherein any of the various $R_1$ groups may be the same as or different from any of the other $R_1$ groups;
$R_2$ is selected from the group consisting of carnosine, vitamin C, polyphenols, epicatechin, epigallocatechin, epigallocatechin gallate, gallic acid, a fluorescent probe, coumarin 6, fluorescein, or a chemotherapeutic compound.

13. The nanoparticle of claim 7, wherein n is an integer from 2 to 5.

14. The plurality of nanoparticles of claim 8, wherein n is an integer from 2 to 5.

15. The method of claim 9, wherein n is an integer from 2 to 5.

16. The method of claim 10, wherein n is an integer from 2 to 5.

17. The compound of claim 12, wherein n is an integer from 2 to 5.

* * * * *